United States Patent
Kim et al.

(10) Patent No.: US 11,246,493 B2
(45) Date of Patent: Feb. 15, 2022

(54) WRIST TEMPERATURE RHYTHM ACQUISITION APPARATUS AND METHOD, CORE TEMPERATURE RHYTHM ACQUISITION APPARATUS AND METHOD, AND WEARABLE DEVICE

(71) Applicants: SAMSUNG ELECTRONICS CO., LTD., Suwon-si (KR); SEOUL NATIONAL UNIVERSITY R&DB FOUNDATION, Seoul (KR)

(72) Inventors: Youn Ho Kim, Hwaseong-si (KR); Kwang Suk Park, Seoul (KR); Soo Young Sim, Seoul (KR); Seung Woo Noh, Seongnam-si (KR); Sang Yun Park, Hwaseong-si (KR); Kwang Min Joo, Seoul (KR); Myung Jun Koh, Gwangju (KR); Hyo Sun Jeon, Seoul (KR)

(73) Assignees: SAMSUNG ELECTRONICS CO., LTD., Suwon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 642 days.

(21) Appl. No.: 15/439,406

(22) Filed: Feb. 22, 2017

(65) Prior Publication Data
US 2018/0092545 A1   Apr. 5, 2018

(30) Foreign Application Priority Data
Sep. 30, 2016   (KR) .................. 10-2016-0126667

(51) Int. Cl.
*A61B 5/01*   (2006.01)
*A61B 5/00*   (2006.01)
(Continued)

(52) U.S. Cl.
CPC ............ *A61B 5/01* (2013.01); *A61B 5/02055* (2013.01); *A61B 5/4857* (2013.01); *A61B 5/681* (2013.01);
(Continued)

(58) Field of Classification Search
None
See application file for complete search history.

(56) References Cited

U.S. PATENT DOCUMENTS

| 6,151,968 A | 11/2000 | Chou |
| 7,083,573 B2 | 8/2006 | Yamakoshi et al. |

(Continued)

FOREIGN PATENT DOCUMENTS

| EP | 2574275 A2 | 4/2013 |
| JP | 5-3877 A | 1/1993 |

(Continued)

OTHER PUBLICATIONS

Communication dated Oct. 24, 2017, issued by the European Patent Office in counterpart European Application No. 17167232.2.
(Continued)

*Primary Examiner* — Matthew Kremer
(74) *Attorney, Agent, or Firm* — Sughrue Mion, PLLC

(57) ABSTRACT

A wrist temperature rhythm acquisition apparatus and method, a core temperature rhythm acquisition apparatus and method, and a wearable device are provided. The wrist temperature rhythm acquisition apparatus includes a data acquirer configured to acquire wrist temperature data of a user and external environment temperature data; and a processor configured to estimate wrist temperature rhythm data in which an influence of an external environment temperature is corrected, based on the acquired wrist temperature data and the acquired external environment temperature data.

9 Claims, 12 Drawing Sheets

(51) Int. Cl.
  *A61B 5/0205* (2006.01)
  *G16H 40/63* (2018.01)
  *A61B 5/024* (2006.01)
  *A61B 5/11* (2006.01)

(52) U.S. Cl.
  CPC .......... *A61B 5/6824* (2013.01); *A61B 5/7221* (2013.01); *A61B 5/7264* (2013.01); *A61B 5/7275* (2013.01); *A61B 5/02438* (2013.01); *A61B 5/1118* (2013.01); *A61B 2560/0242* (2013.01); *G16H 40/63* (2018.01)

(56) References Cited

U.S. PATENT DOCUMENTS

| | | | |
|---|---|---|---|
| 7,162,058 B2 | 1/2007 | Mimura et al. | |
| 7,457,442 B2 | 11/2008 | Mimura et al. | |
| 8,936,552 B2 | 1/2015 | Kateraas et al. | |
| 2003/0235817 A1* | 12/2003 | Bartkowiak | A61B 5/14532 435/5 |
| 2005/0245839 A1 | 11/2005 | Stivoric et al. | |
| 2006/0195035 A1* | 8/2006 | Sun | A61B 5/02116 600/503 |
| 2007/0077079 A1* | 4/2007 | Kim | G03G 15/0266 399/44 |
| 2008/0161715 A1 | 7/2008 | Stivoric et al. | |
| 2008/0167572 A1 | 7/2008 | Stivoric et al. | |
| 2008/0167573 A1 | 7/2008 | Stivoric et al. | |
| 2008/0214949 A1 | 9/2008 | Stivoric et al. | |
| 2009/0198112 A1* | 8/2009 | Park | A61B 5/02438 600/301 |
| 2010/0280331 A1* | 11/2010 | Kaufman | A61B 5/01 600/301 |
| 2012/0068848 A1* | 3/2012 | Campbell | A61B 5/0008 340/573.1 |
| 2012/0319847 A1 | 12/2012 | Heller | |
| 2013/0072765 A1 | 3/2013 | Kahn et al. | |
| 2014/0129010 A1* | 5/2014 | Garg | G06F 17/00 700/94 |
| 2014/0247136 A1* | 9/2014 | Proud | G08C 17/02 340/870.01 |
| 2014/0311209 A1 | 10/2014 | Niederberger et al. | |
| 2014/0321503 A1 | 10/2014 | Niederberger et al. | |
| 2014/0368474 A1 | 12/2014 | Kim et al. | |
| 2015/0057963 A1 | 2/2015 | Zakharov et al. | |
| 2015/0272452 A1* | 10/2015 | Mullin | A61B 5/02422 600/301 |
| 2015/0335282 A1 | 11/2015 | Lee | |
| 2016/0058389 A1 | 3/2016 | Lee et al. | |
| 2016/0071393 A1* | 3/2016 | Kaplan | A61B 5/6831 340/539.12 |
| 2016/0143630 A1* | 5/2016 | Pardey | A61B 10/0012 600/549 |
| 2016/0367187 A1* | 12/2016 | Ahmed | A61B 5/02405 |
| 2017/0215741 A1* | 8/2017 | Auer | G01K 13/004 |
| 2017/0249824 A1 | 8/2017 | Kaplan et al. | |

FOREIGN PATENT DOCUMENTS

| | | |
|---|---|---|
| JP | 53876 A | 1/1993 |
| KR | 10-1179997 B1 | 9/2012 |
| KR | 10-2014-0146346 A | 12/2014 |
| KR | 10-1525330 B1 | 6/2015 |
| KR | 10-1564073 B1 | 10/2015 |
| KR | 10-2016-0025285 A | 3/2016 |
| KR | 10-1622040 B1 | 6/2016 |
| WO | 01/93053 A1 | 12/2001 |
| WO | 2013043747 A1 | 3/2013 |
| WO | 2013/169014 A1 | 11/2013 |
| WO | 2015025311 A1 | 2/2015 |
| WO | 2016040281 A1 | 3/2016 |

OTHER PUBLICATIONS

Seung-hwan Park et al., "Development of Hybrid Temperature Measurement System for Bio-signal Application Device", Journal of Korean Institute of Information Technology 6(6), Korean Institute of Information Technology, 2008.12, (pp. 195-202, 9 Pages total) http://www.dbpia.co.kr/Article/NODE01102820.

J.A. Sarabia et al., "Circadian rhythm of wrist temperature in normal-living subjects A candidate of new index of the circadian system", Physiology & Behavior 95 (2008), pp. 570-580, 2008 Elsevier Inc, doi:10.1016/j.physbeh.2008.08.005.

\* cited by examiner

FIG. 3

| TIME(min) | ... | t10 | t11 | t12 | t13 | t14 | t15 | t16 | t17 | t18 | ... | t47 | t48 | t49 | t50 | ... |
|---|---|---|---|---|---|---|---|---|---|---|---|---|---|---|---|---|
| WRIST TEMPERATURE DATA(°C) | ... | 34.5 | 34.5 | 34.8 | 34.8 | 34.7 | 34.6 | 34.5 | 34.7 | 35.3 | ... | 34.9 | 35 | 35 | 34.7 | ... |
| EXTERNAL ENVIRONMENT TEMPERATURE DATA(°C) | ... | 28.1 | 28.1 | 28.6 | 28.6 | 28.5 | 28.5 | 28.5 | 28.5 | 30.0 | ... | 30.2 | 30.2 | 29.5 | 28.8 | ... |
| REMAINING WRIST TEMPERATURE DATA(°C) | ... | 34.5 | - | - | - | - | - | 34.5 | - | - | ... | - | 35 | - | - | ... |
| INTERPOLATED WRIST TEMPERATURE DATA(°C) | ... |  | 34.5 | 34.5 | 34.5 | 34.5 | 34.5 |  | 34.5 | 34.5 | ... | 35 |  | 35 | 35 | ... |
| WRIST TEMPERATURE RHYTHM DATA(°C) | ... | 34.5 | 34.5 | 34.5 | 34.5 | 34.5 | 34.5 | 34.5 | 34.5 | 34.5 | ... | 35 | 35 | 35 | 35 | ... |

WRIST TEMPERATURE RHYTHM ACQUISITION APPARATUS AND METHOD, CORE TEMPERATURE RHYTHM ACQUISITION APPARATUS AND METHOD, AND WEARABLE DEVICE

CROSS-REFERENCE TO RELATED APPLICATION

This application claims priority from Korean Patent Application No. 10-2016-0126667, filed on Sep. 30, 2016, in the Korean Intellectual Property Office, the disclosure of which is incorporated herein by reference in its entirety.

BACKGROUND

1. Field

Apparatuses and methods consistent with example embodiments relate to a wrist temperature rhythm acquisition apparatus and method, a core temperature rhythm acquisition apparatus and method and a wrist-wearable device employing a wrist temperature rhythm acquisition technique and a core temperature rhythm acquisition technique.

2. Description of Related Art

The rhythm of the wrist temperature reflects the rhythm of the biological clock in the human body. That is, the rhythm of the wrist temperature is inversely related to the daily cyclic rhythm of the core temperature. The core temperature is an archetypal biometric signal for observing a daily cyclic rhythm, and the daily cyclic rhythm of the core temperature provides various types of health information, such as brain disease, sleep disorder, a woman's menstrual cycle, and the like. Long-term monitoring is performed to measure the daily cyclic rhythm of the core temperature, but general invasive methods are not suitable for the long-term monitoring.

On the other hand, a wrist temperature that reflects the core temperature can be monitored non-invasively, and hence it is suitable for the long-term monitoring. However, the wrist temperature is significantly affected by an external environment, and thus a technology that can acquire a rhythm of wrist temperature by eliminating the influence of external environment is being developed.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, there is provided a wrist temperature rhythm acquisition apparatus including a data acquirer configured to acquire wrist temperature data of a user and external environment temperature data, and a processor configured to estimate wrist temperature rhythm data in which an influence of an external environment temperature is corrected, based on the acquired wrist temperature data and the acquired external environment temperature data.

The processor may be further configured to determine an amount of change in a wrist temperature per unit time and an amount of change in the external environment temperature per unit time, based on the acquired wrist temperature data and the acquired external environment temperature data, and determine whether the determined amount of change in the wrist temperature per unit time and the determined amount of change in the external environment temperature per unit time satisfy a first condition or a second condition. The processor may be further configured to remove first wrist temperature data in a predetermined time range from the acquired wrist temperature data to generate remaining wrist temperature data, in response to the determined amount of change in the wrist temperature per unit time and the determined amount of change in the external environment temperature per unit time satisfying the first condition or the second condition, and estimate the wrist temperature rhythm data in which the influence of the external environment temperature is corrected by interpolating the removed first wrist temperature data based on the remaining wrist temperature data.

The first condition may be that the amount of change in the wrist temperature per unit time is less than a first threshold and the amount of change in the external environment temperature per unit time that corresponds to the amount of change in the wrist temperature per unit time is less than a second threshold, or that the amount of change in the wrist temperature per unit time is greater than a third threshold and the amount of change in the external environment temperature per unit time that corresponds to the amount of change in the wrist temperature per unit time is greater than a fourth threshold.

The second condition may be that an absolute value of the amount of change in the external environment temperature per unit time is greater than a fifth threshold.

The processor may be further configured to, in response to the determined amount of change in the wrist temperature per unit time and the determined amount of change in the external environment temperature per unit time satisfying the first condition, remove second wrist temperature data in a time unit, from the acquired wrist temperature data, remove third wrist temperature data in a first time range, from the acquired wrist temperature data, based on a reference time point for determining the amount of change in the wrist temperature per unit time, or remove fourth wrist temperature data in the first time range before and after the reference time point for determining the amount of change in the wrist temperature per unit time, from the acquired wrist temperature data.

The processor may be further configured to, in response to the determined amount of change in the wrist temperature per unit time and the determined amount of change in the external environment temperature per unit time satisfying the second condition, remove fifth wrist temperature data in a second time range, from the acquired wrist temperature data, based on the reference time point for determining the amount of change in the wrist temperature per unit time, or remove sixth wrist temperature data in the second time range before and after the reference time point for determining the amount of change in the wrist temperature per unit time, from the acquired wrist temperature data.

According to an aspect of an example embodiment, there is provided a core temperature rhythm acquisition apparatus including a data acquirer configured to acquire wrist temperature data of a user, external environment temperature data, heart rate data of the user, and data of an amount of exercise that the user carried out, and a processor configured to estimate wrist temperature rhythm data in which an influence of an external environment temperature is corrected, based on the acquired wrist temperature data and the acquired external environment temperature data, and estimate core temperature rhythm data, based on the estimated wrist temperature rhythm data, the acquired heart rate data, and the acquired data of the amount of exercise.

The processor may be further configured to determine an amount of change in a wrist temperature per unit time and an amount of change in the external environment temperature per unit time, based on the acquired wrist temperature data and the acquired external environment temperature data, determine whether the determined amount of change in the wrist temperature per unit time and the determined amount of change in the external environment temperature per unit time satisfy a first condition or a second condition, remove first wrist temperature data in a predetermined time range from the acquired wrist temperature data to generate remaining wrist temperature data, in response to the determined amount of change in the wrist temperature per unit time and the determined amount of change in the external environment temperature per unit time satisfying the first condition or the second condition, and estimate the wrist temperature rhythm data in which the influence of the external environment temperature is corrected by interpolating the removed first wrist temperature data based on the remaining wrist temperature data.

The first condition may be that the amount of change in the wrist temperature per unit time is less than a first threshold and the amount of change in the external environment temperature per unit time that corresponds to the amount of change in the wrist temperature per unit time is less than a second threshold, or that the amount of change in the wrist temperature per unit time is greater than a third threshold and the amount of change in the external environment temperature per unit time that corresponds to the amount of change in the wrist temperature per unit time is greater than a fourth threshold.

The second condition may be that an absolute value of the amount of change in the external environment temperature per unit time is greater than a fifth threshold.

The processor may be further configured to, in response to the determined amount of change in the wrist temperature per unit time and the determined amount of change in the external environment temperature per unit time satisfying the first condition, remove second wrist temperature data in a time unit, from the acquired wrist temperature data, remove third wrist temperature data in a first time range, from the acquired wrist temperature data, based on a reference time point for determining the amount of change in the wrist temperature per unit time, or remove fourth wrist temperature data in the first time range before and after the reference time point for determining the amount of change in the wrist temperature per unit time, from the acquired wrist temperature data.

The processor may be further configured to, in response to the determined amount of change in the wrist temperature per unit time and the determined amount of change in the external environment temperature per unit time satisfying the second condition, remove fifth wrist temperature data in a second time range, from the acquired wrist temperature data, based on the reference time point for determining the amount of change in the wrist temperature per unit time, or remove sixth wrist temperature data in the second time range before and after the reference time point for determining the amount of change in the wrist temperature per unit time, from the acquired wrist temperature data.

The processor may be further configured to estimate the core temperature rhythm data, using a core temperature rhythm estimation model.

The core temperature rhythm estimation model may be generated through machine learning based on core temperature rhythm training data, wrist temperature rhythm training data corresponding to the core temperature rhythm training data, heart rate training data, and training data of an amount of exercise.

The machine learning may include any one or any combination of a neural network, a decision tree, a genetic algorithm, genetic programming, a k-nearest neighbor algorithm, a radial basis function network, a random forest, a support vector machine, and deep learning.

According to an aspect of an example embodiment, there is provided a method including acquiring wrist temperature data of a user and external environment temperature data, and estimating wrist temperature rhythm data in which an influence of an external environment temperature is corrected, based on the acquired wrist temperature data and the acquired external environment temperature data.

The estimating of the wrist temperature rhythm data may include determining an amount of change in a wrist temperature per unit time and an amount of change in the external environment temperature per unit time, based on the acquired wrist temperature data and the acquired external environment temperature data, determining whether the determined amount of change in the wrist temperature per unit time and the determined amount of change in the external environment temperature per unit time satisfy a first condition or a second condition. The estimating of the wrist temperature rhythm data may further include removing first wrist temperature data in a predetermined time range from the acquired wrist temperature data to generate remaining wrist temperature data, in response to the determined amount of change in the wrist temperature per unit time and the determined amount of change in the external environment temperature per unit time satisfying the first condition or the second condition, and estimating the wrist temperature rhythm data in which the influence of the external environment temperature is corrected by interpolating the removed first wrist temperature data based on the remaining wrist temperature data.

The first condition may be that the amount of change in the wrist temperature per unit time is less than a first threshold and the amount of change in the external environment temperature per unit time that corresponds to the amount of change in the wrist temperature per unit time is less than a second threshold, or that the amount of change in the wrist temperature per unit time is greater than a third threshold and the amount of change in the external environment temperature per unit time that corresponds to the amount of change in the wrist temperature per unit time is greater than a fourth threshold.

The second condition may be that an absolute value of the amount of change in the external environment temperature per unit time is greater than a fifth threshold.

The removing of the first wrist temperature data may include, in response to the determined amount of change in the wrist temperature per unit time and the determined amount of change in the external environment temperature per unit time satisfying the first condition, removing second wrist temperature data in a time unit, from the acquired wrist temperature data, removing third wrist temperature data in a first time range, from the acquired wrist temperature data, based on a reference time point for determining the amount of change in the wrist temperature per unit time, or removing fourth wrist temperature data in the first time range before and after the reference time point for determining the amount of change in the wrist temperature per unit time, from the acquired wrist temperature data.

The removing of the first wrist temperature data may include, in response to the determined amount of change in the wrist temperature per unit time and the determined amount of change in the external environment temperature per unit time satisfying the second condition, removing fifth wrist temperature data in a second time range, from the acquired wrist temperature data, based on the reference time point for determining the amount of change in the wrist temperature per unit time, or removing sixth wrist temperature data in the second time range before and after the reference time point for determining the amount of change in the wrist temperature per unit time, from the acquired wrist temperature data.

The method may further include acquiring heart rate data of the user and data of an amount of exercise that the user carried out, and estimating core temperature rhythm data, based on the estimated wrist temperature rhythm data, the acquired heart rate data, and the acquired data of the amount of exercise.

The estimating of the core temperature rhythm may include estimating the core temperature rhythm data, using a core temperature rhythm estimation model.

The core temperature rhythm estimation model may be generated through machine learning based on core temperature rhythm training data, wrist temperature rhythm training data corresponding to the core temperature rhythm training data, heart rate training data, and training data of an amount of exercise.

According to an aspect of an example embodiment, there is provided a wrist-wearable device including a first sensor configured to sense wrist temperature data of a user, a second sensor configured to sense external environment temperature data, and a processor configured to acquire wrist temperature rhythm data in which an influence of an external environment temperature is corrected, based on the sensed wrist temperature data and the sensed external environment temperature data.

The first sensor may be disposed on a surface of the wrist-wearable device in proximate contact with a wrist of the user when the wrist-wearable device is worn by the user.

The second sensor may be disposed on a surface of the wrist-wearable device that is not in proximate contact with a wrist of the user when the wrist-wearable device is worn by the user.

The processor may be further configured to determine an amount of change in a wrist temperature per unit time and an amount of change in the external environment temperature per unit time, based on the sensed wrist temperature data and the sensed external environment temperature data, and determine whether the determined amount of change in the wrist temperature per unit time and the determined amount of change in the external environment temperature per unit time satisfy a first condition or a second condition. The processor may be further configured to remove first wrist temperature data in a predetermined time range from the sensed wrist temperature data to generate remaining wrist temperature data, in response to the determined amount of change in the wrist temperature per unit time and the determined amount of change in the external environment temperature per unit time satisfying the first condition or the second condition, and acquire the wrist temperature rhythm data in which the influence of the external environment temperature is corrected by interpolating the removed first wrist temperature data based on the remaining wrist temperature data.

The processor may be further configured to, in response to the determined amount of change in the wrist temperature per unit time and the determined amount of change in the external environment temperature per unit time satisfying the first condition, remove second wrist temperature data in a time unit, from the sensed wrist temperature data, remove third wrist temperature data in a first time range, from the sensed wrist temperature data, based on a reference time point for determining the amount of change in the wrist temperature per unit time, or remove fourth wrist temperature data in the first time range before and after the reference time point for determining the amount of change in the wrist temperature per unit time, from the sensed wrist temperature data, and in response to the determined amount of change in the wrist temperature per unit time and the determined amount of change in the external environment temperature per unit time satisfying the second condition, remove fifth wrist temperature data in a second time range, from the sensed wrist temperature data, based on the reference time point for determining the amount of change in the wrist temperature per unit time, or remove sixth wrist temperature data in the second time range before and after the reference time point for determining the amount of change in the wrist temperature per unit time, from the sensed wrist temperature data.

The wrist-wearable device may further include a third sensor configured to sense heart rate data of the user, and a fourth sensor configured to sense data of an amount of exercise that the user carried out. The processor may be further configured to acquire core temperature rhythm data, based on the acquired wrist temperature rhythm data, the sensed heart rate data, and the sensed data of the amount of exercise.

The processor may be further configured to acquire the core temperature rhythm data, using a core temperature rhythm estimation model.

The core temperature rhythm estimation model may be generated through machine learning based on core temperature rhythm training data, wrist temperature rhythm training data corresponding to the core temperature rhythm training data, heart rate training data, and training data of an amount of exercise.

According to an aspect of an example embodiment, there is provided an apparatus including a first sensor configured to sense user temperatures, a second sensor configured to sense external environment temperatures, and a processor configured to remove one or more first user temperatures in a predetermined time range from the sensed user temperatures to generate remaining user temperatures, in response to an amount of change in the sensed user temperatures per unit time and an amount of change in the sensed external environment temperatures per unit time being outside respective threshold ranges, and interpolate, into the remaining user temperatures, one or more second user temperatures replacing the removed one or more first user temperatures, based on the remaining user temperatures, to generate user temperature rhythm data.

The apparatus may further include a third sensor configured to sense heart rates of the user, and a fourth sensor configured to sense amounts of exercise that the user carried out. The processor may be further configured to generate core temperature rhythm data, based on the generated user temperature rhythm data, the sensed heart rates, and the sensed amounts of exercise.

BRIEF DESCRIPTION OF THE DRAWINGS

The above and/or other aspects will be more apparent by describing example embodiments with reference to the accompanying drawings.

FIG. 3 is a table for describing a process of acquiring a wrist temperature rhythm, according to an example embodiment.

Figure 1:
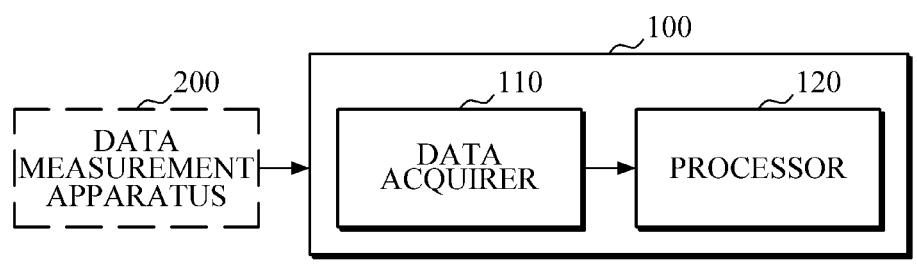
FIG. 1 is a block diagram illustrating a wrist temperature rhythm acquisition apparatus according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

In addition, the terms such as "unit," "-er (-or)," and "module" described in the specification refer to an element for performing at least one function or operation, and may be implemented in hardware, software, or the combination of hardware and software.

FIG. 1 is a block diagram illustrating a wrist temperature rhythm acquisition apparatus 100 according to an example embodiment. The wrist temperature rhythm acquisition apparatus 100 may be an apparatus for acquiring a wrist temperature rhythm in which the influence of external environment temperature is corrected. The wrist temperature rhythm acquisition apparatus 100 may be implemented by a software module or manufactured in the form of a hardware chip, and be mounted in an electronic device. In this case, the electronic device may include a mobile phone, a smartphone, a tablet computer, a notebook computer, a personal digital assistant (PDA), a portable multimedia player (PMP), a navigation system, an MP3 player, a digital camera, a wearable device, etc. The type of wearable device may include a wristwatch type, a wrist band type, a belt type, a necklace type, an ankle band type, a thigh band type, a forearm band type, etc. However, the electronic device may not be limited to the above example, and the wearable device may also not be limited to the above example.

Referring to FIG. 1, the wrist temperature rhythm acquisition apparatus 100 includes a data acquirer 110 and a processor 120.

The data acquirer 110 may acquire wrist temperature data of a user and external environment temperature data.

According to an example embodiment, the data acquirer 110 may receive the wrist temperature data of the user and the external environment temperature data from a data measurement apparatus 200 using a communication technology. The communication technology may include a Bluetooth communication, Bluetooth low energy (BLE) communication, a near-field commutation (NFC), a wireless local area network (WLAN) communication, a ZigBee communication, an infrared data association (IrDA) communication, a Wi-Fi direct (WFD) communication, a ultra-wideband (UWB) communication, an Ant+ communication, a Wi-Fi communication, a radio frequency identification (RFID) communication, a 3G communication, a 4G communication, a 5G communication, and the like, but is not limited thereto.

The processor 120 may estimate wrist temperature rhythm data in which the influence of external environment temperature is corrected on the basis of the wrist temperature data and the external environment temperature data.

For example, the processor 120 may remove wrist temperature data in a predetermined range from the entire wrist temperature data, according to whether the amount of change in the wrist temperature per unit of time and/or the amount of change in external environment temperature per unit of time satisfy a predetermined condition. The processor 120 may further interpolate the removed wrist temperature data to estimate the wrist temperature rhythm data in which the influence of external environment temperature is corrected.

The processor 120 will be described below in more detail with reference to FIG. 2.

The data measurement apparatus 200 may measure the wrist temperature data of the user and the external environment temperature data in response to a control signal. For example, the data measurement apparatus 200 may operate various internal sensors to measure the user's wrist temperature data and the external environment temperature data in response to a control signal generated according to a user input or a control signal received from the wrist temperature rhythm acquisition apparatus 100.

The data measurement apparatus 200 may have a communication interface mounted therein for wired/wireless communication and transmit the user's wrist temperature data and the external environment temperature data to the data acquirer 110.

The data measurement apparatus 200 may be a wearable device that can be worn on a user's body part. However, this is an example, and the data measurement apparatus 200 is not limited to the wearable device. That is, with regard to the type of the data measurement apparatus 200, the size or portability of the apparatus is not particularly limited.

Figure 2:
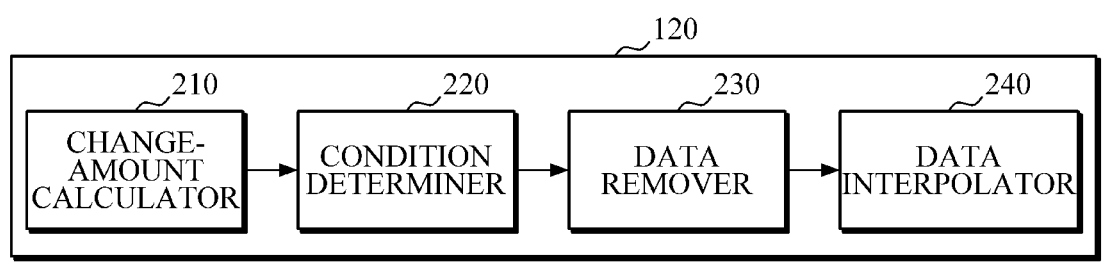
FIG. 2 is a block diagram illustrating a processor according to an example embodiment.

FIG. 2 is a block diagram illustrating the processor 120 according to an example embodiment.

Referring to FIG. 2, the processor 120 includes a change-amount calculator 210, a condition determiner 220, a data remover 230, and a data interpolator 240.

The change-amount calculator 210 may calculate the amount of change in wrist temperature per unit of time on the basis of wrist temperature data and calculate the amount of change in external environment temperature on the basis of external environment temperature data. In this case, the unit of time may be one minute, which is an example embodiment, and the unit of time is not limited thereto. That is, the unit of time may be set to various values, such as 2 minutes, 5 minutes, 1 hour, and the like, according to the performance or purpose of a system.

The condition determiner 220 may determine whether the measured amount of change in wrist temperature per unit of time (hereinafter, will be referred to as an "amount of change in wrist temperature per unit time") and the measured amount of change in external environment temperature per unit of time (hereinafter, will be referred to as an "amount of change in external environment temperature per unit time") satisfy a predetermined condition. In this case, the predetermined condition may include a first condition and a second condition.

According to an example embodiment, the first condition may be that the amount of change in wrist temperature per unit time is less than a first threshold and the amount of change in external environment temperature per unit time that corresponds to the amount of change in wrist temperature per unit time is less than a second threshold, or that the amount of change in wrist temperature per unit time exceeds a third threshold and the amount of change in external environment temperature per unit time that corresponds to the amount of change in wrist temperature per unit time exceeds a fourth threshold. In this case, the first threshold may be 0, the second threshold may be 0.1, the third threshold may be 0, and the fourth threshold may be 0.2, but these are only examples, and the thresholds are not limited thereto. That is, the first to fourth thresholds may be set to various values according to the unit of time and the performance or purpose of the system.

According to an example embodiment, the second condition may be that an absolute value of the amount of change in external environment temperature per unit time exceeds a fifth threshold. In this case, the fifth threshold may be 0.9, which is an example embodiment, and is not limited thereto. That is, the fifth threshold may be set to various values according to the unit of time and the performance or purpose of the system.

The data remover 230 may remove wrist temperature data in a predetermined range from the entre wrist temperature data when the amount of change in wrist temperature per unit time and the amount of change in external environment temperature per unit time satisfy the predetermined condition.

According to an example embodiment, when the amount of change in wrist temperature per unit time and the amount of change in external environment temperature per unit time satisfy the first condition, the data remover 230 may remove the wrist temperature data in a relevant unit time from the entire wrist temperature data. For example, in the case in which the wrist temperature is $T_{wrist}$ (t0) at t=t0, the wrist temperature is $T_{wrist}$ (t0+1 minute) at t=t0+1 minute (1 minute corresponds to a unit of time), the environment temperature is $T_{environment}$ (t0) at t=t0, and the wrist temperature is $T_{environment}$ (t0+1) at t=t0+1 minute, the amount of change in wrist temperature during the period from t0 to t0+1 minute is $\Delta T_{wrist}=T_{wrist}$ (t0+1) $T_{wrist}$ (t0), and the amount of change in external environment temperature during the period from t0 and t0+1 minute is $\Delta T_{environment}=T_{environment}$ (t0+1)−$T_{environment}$ (t0). When $\Delta T_{wrist}$ and $\Delta T_{environment}$ satisfy the first condition, the data remover 230 may remove the wrist temperature data between t0 and t0+1 minute from the entire wrists temperature data.

According to another example embodiment, when the amount of change in wrist temperature per unit time and the amount of change in external environment temperature per unit time satisfy the first condition, the data remover 230 may remove the wrist temperature data in a first time range after a reference time point for calculating the amount of change from the entire wrist temperature data. In this case, the first time range may be five minutes, which is an example embodiment, and may not be limited thereto. That is, the first time range may be set to various values according to the unit of time and the performance or purpose of the system. For example, the data remover 230 may remove the wrist temperature data between t0 and t0+5 minutes from the entire wrist temperature data in the above example.

According to still another example embodiment, when the amount of change in wrist temperature per unit time and the amount of change in external environment temperature per unit time satisfy the first condition, the data remover 230 may remove the wrist temperature data in the first time range before and after a reference time point for calculating the amount of change from the entire wrist temperature data. For example, the data remover 230 may remove the wrist temperature data between t0−2.5 minutes and t0+2.5 minutes from the entire wrist temperature data.

According to yet another example embodiment, when the amount of change in external environment temperature per unit time satisfies a second condition, the data remover 230 may remove wrists temperature data in a second time range after the reference time point for calculating the amount of change. In this case, the second time range may be 30 minutes, which is an example embodiment, and may not be limited thereto. That is, the second time range may be set to various values according to the unit of the time and the performance or purpose of the system. For example, when the external environment temperature is $T_{environment}$ (t0) at t=t0 and the external environment temperature is $T_{environment}$ (t0+1) at t=t0+1 minute, the amount of change in external environment temperature during the period from t0 to t0+1 minute is $\Delta T_{environment}=T_{environment}$ (t0+1)−$T_{environment}$ (t0). When $\Delta T_{environment}$ satisfies the second condition, the data remover 230 may remove the wrist temperature data between t0 and t0+1 minute from the entire wrist temperature data.

According to another example embodiment, when the amount of change in external environment temperature per unit time satisfies the second condition, the data remover 230 may remove the wrist temperature data in the second time range before and after the reference time point for calculating the amount of change. For example, the data remover 230 may remove the wrist temperature data between t0−15 minutes and t0+15 minutes from the entire wrist temperature data in the above example.

The data interpolator 240 may interpolate the wrist temperature data removed by the data remover 230 and estimate the wrist temperature rhythm data in which the influence of external environment temperature is corrected. For example, the data interpolator 240 may interpolate the removed wrist temperature data on the basis of the remaining wrist temperature data resulting from the removal. In this case, the data interpolator 240 may use various interpolation techniques, such as linear interpolation, double linear interpolation, parabolic interpolation, polynomial interpolation, spline interpolation, and the like.

FIG. 3 is a table for describing a process of acquiring a wrist temperature rhythm, according to an example embodiment. An example shown in FIG. 3 assumes that a unit of time is 1 minute, wrist temperature data and external environment temperature data are measured at intervals of 1 minute, a first threshold is 0, a second threshold is 0.1, a third threshold is 0, a fourth threshold is 0.2, and a fifth threshold is 0.9. In addition, the example also assumes that a first time range is 5 minutes and a second time range is 30 minutes.

Referring to FIGS. 2 and 3, the change-amount calculator 210 calculates 0° C./min as the amount of change in wrist temperature during the period from t10 to t11 and 0° C./min as the amount of change in external environment temperature during the same period. The condition determiner 220 determines whether, the amount of change in wrist temperature, 0° C./min, and the amount of change in external environment temperature, 0° C./min, satisfy a first condition or a second condition, and confirms that the amount of change in wrist temperature and the amount of change in external environment temperature during the period from t10 to t11 do not satisfy the first condition or the second condition.

The change-amount calculator 210 calculates 0.3° C./min as the amount of change in wrist temperature during the period from t11 to t12 and 0.5° C./min as the amount of change in external environment temperature during the same period. Because the amount of change in wrist temperature, 0.1° C./min, exceeds the third threshold, 0, and the amount of change in external environment temperature, 0.5° C./min, exceeds the fourth threshold, 0.2, the condition determiner 220 determines that the amount of change in wrist temperature and the amount of change in external environment temperature during the period from t11 to t12 satisfy the first condition. As the amount of change in wrist temperature and the amount of change in external environment temperature satisfy the first condition, the data remover 230 removes the wrist temperature data 34.5, 34.6, 34.6, 34.5, and 34.5 of 5 minutes from t11 to t15.

The change-amount calculator 210 calculates 0.2° C./min as the amount of change in wrist temperature during the period from t16 to t17 and 0° C./min as the amount of change in external environment temperature during the same period. The condition determiner 220 determines whether the amount of change in wrist temperature, 0.2° C./min, and the amount of change in external environment temperature, 0° C./min, satisfy the first condition or the second condition, and confirms that the amount of change in wrist temperature and the amount of change in external environment temperature during the period from t16 to t17 do not satisfy the first condition or the second condition.

The change-amount calculator 210 calculates 0.6° C./min as the amount of change in wrist temperature during the period from t17 to t18 and 1.5° C./min as the amount of change in external environment temperature during the same period. Because an absolute value, 1.5, of the amount of change in external environment temperature exceeds the fifth threshold, 0.9, the condition determiner 220 determines that the amount of change in external environment temperature during the period from t17 to t18 satisfy the second condition. Because the amount of change in external environment temperature during the period from t17 to t18 satisfies the second condition, the data remover 230 removes the wrist temperature data 34.7 to 34.9 of 30 minutes from t17 to t47.

The change-amount calculator 210 calculates 0° C./min as the amount of change in wrist temperature during the period from t48 to t49 and −0.7° C./min as the amount of change in external environment temperature during the same period. The condition determiner 220 determines whether the amount of change in wrist temperature, 0° C./min, and the amount of change in external environment temperature, −0.7° C./min, satisfy the first condition or the second condition, and confirms that the amount of change in wrist temperature and the amount of change in external environment temperature during the period from t48 to t49 do not satisfy the first condition or the second condition.

The change-amount calculator 210 calculates −0.3° C./min as the amount of change in wrist temperature during the period from t49 to t50 and 0.7° C./min as the amount of change in external environment temperature during the same period. Because the amount of change in wrist temperature, −0.3° C./min, is less than the first threshold, 0, and the amount of change in external environment temperature, −0.7° C./min, is less than the second threshold, 0.1, the condition determiner 220 determines that the amount of change in wrist temperature and the amount of change in external environment temperature during the time period from t49 to t50 satisfy the first condition. Because the amount of change in wrist temperature and the amount of change in external environment temperature during the time period from t49 to t50 satisfy the first condition, the data remover 230 removes the wrist temperature data 35, 34.7, etc. of 5 minutes from t49 to t54.

The data interpolator 240 estimates wrist temperature rhythm data by interpolating the removed wrist temperature data $T_{wrist}(t11)$ to $T_{wrist}(t15)$, $T_{wrist}(t17)$ to $T_{wrist}(t47)$, $T_{wrist}(t49)$ to $T_{wrist}(t54)$, etc. on the basis of the remaining wrist temperature data $T_{wrist}(t10)=34.5°$ C., $T_{wrist}(t16)=34.5°$ C., $T_{wrist}(t48)=35°$ C., etc.

Figure 4:
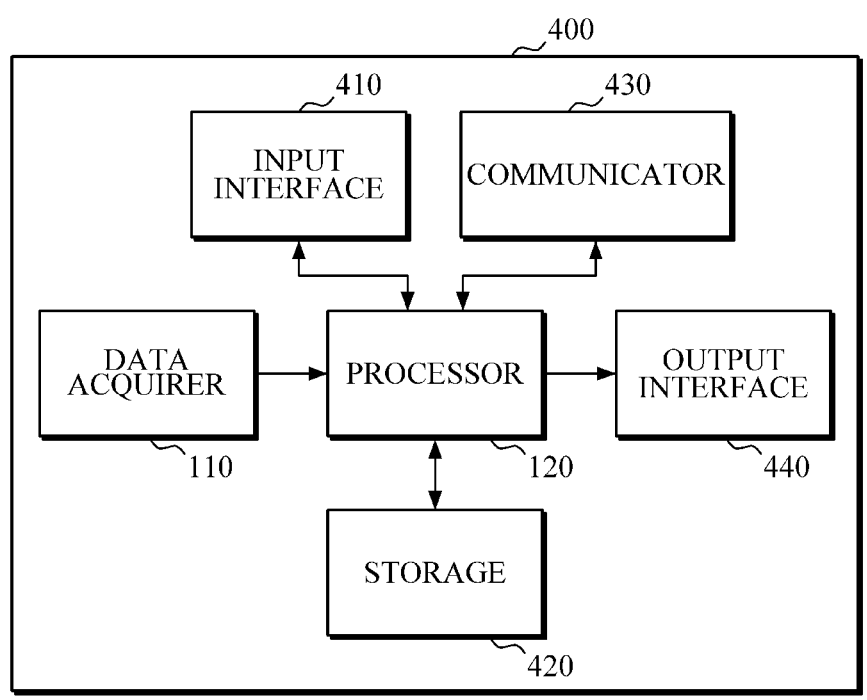
FIG. 4 is a block diagram illustrating a wrist temperature rhythm acquisition apparatus according to another example embodiment.

FIG. 4 is a block diagram illustrating a wrist temperature rhythm acquisition apparatus 400 according to another example embodiment.

Referring to FIG. 4, the wrist temperature rhythm acquisition apparatus 400 includes an input interface 410, a storage 420, a communicator 430, an output interface 440, a data acquirer 110, and a processor 120. Here, the data acquirer 110 and the processor 120 are the same as those described with reference to FIG. 1, and thus detailed descriptions thereof will be omitted.

The input interface 410 may receive various operation signals input from a user. According to an example embodiment, the input interface 410 may include a key pad, a dome switch, a touch pad (resistive/capacitive), a jog switch, a hardware (H/W) button, and the like. When the touch pad forms a mutual layer structure with a display, it may be referred to as a touch screen.

The storage 420 may store a program or instructions for operations of the wrist temperature rhythm acquisition apparatus 400 and may store data input to and/or output from the wrist temperature rhythm acquisition apparatus 400. In addition, the storage 420 may store wrist temperature data and external environment temperature data obtained through the data acquirer 110, the amount of change in wrist temperature per unit time and the amount of change in external environment temperature per unit time that are calculated by the processor 120, wrist temperature rhythm data estimated by the processor 120, and so on.

The storage 420 may include a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, an optical disk, and the like. In addition, the wrist temperature rhythm acquisition apparatus 400 may operate an external storage medium, such as a web storage, which performs the storage function of the storage 420 on the Internet.

The communicator 430 may communicate with an external device. For example, the communicator 430 may transmit the data input from the user through the input interface 410 and the wrist temperature rhythm data estimated by the processor 120 to the external device, and may receive various data helpful for the estimation of wrist temperature rhythm data from the external device.

In this case, the external device may be a medical device that uses the estimated wrist temperature rhythm data, a printer for outputting a result, or a display device that displays the estimated wrist temperature rhythm data. In addition, the external device may be a digital TV, a desktop computer, a mobile phone, a smartphone, a tablet computer, a notebook computer, a PDA, a PMP, a navigation system, an MP3 player, a digital camera, a wearable device, or the like, but is not limited thereto.

The communicator 430 may communicate with the external device, using a Bluetooth communication, a BLE communication, NFC, a WLAN communication, a ZigBee communication, an IrDA communication, a WFD communication, a UWB communication, an Ant+ communication, a Wi-Fi communication, an RFID communication, a 3G communication, a 4G communication, a 5G communication, and the like. However, the above description is provided for the purpose of example, and the type of communication is not limited thereto.

Although the data acquirer 110 and the communicator 430 are illustrated as separate elements in the example of FIG. 4, the data acquirer 110 and the communicator 430 may be integrated into one element.

The output interface 440 may output a result of the estimation of wrist temperature rhythm data, and the like. According to an example embodiment, the output interface 440 may output the result of the estimation of wrist temperature rhythm data and the like in any one or any combination of audible, visual, or tactile manners. For example, the output interface 440 may output the result of the estimation of wrist temperature rhythm data and the like using voice, text, vibration, etc. To this end, the output interface 440 may include a display, a speaker, a vibrator, or the like.

Figure 5:
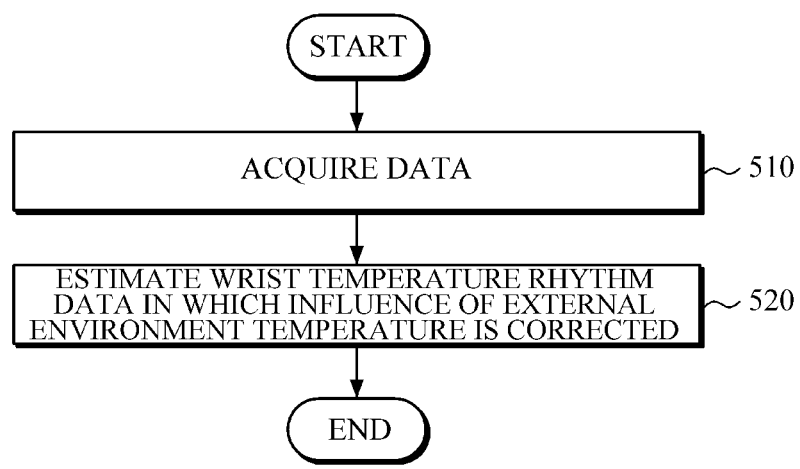
FIG. 5 is a flowchart illustrating a method of an acquiring wrist temperature rhythm, according to an example embodiment.

FIG. 5 is a flowchart illustrating a method of an acquiring wrist temperature rhythm, according to an example embodiment.

Referring to FIGS. 1 and 5, the wrist temperature rhythm acquisition apparatus 100 acquires wrist temperature data of a user and external environment temperature data, as depicted in 510.

According to an example embodiment, the wrist temperature rhythm acquisition apparatus 100 may receive the wrist temperature data of the user and the external environment temperature data from a data measurement apparatus 200, using a communication technology.

The wrist temperature rhythm acquisition apparatus 100 estimates wrist temperature rhythm data in which the influence of external environment temperature is corrected on the basis of the wrist temperature data and the external environment temperature data, as depicted in 520.

For example, the wrist temperature rhythm acquisition apparatus 100 may remove the wrist temperature data in a predetermined range from the entire wrist temperature data according to whether the amount of change in wrist temperature per unit time and/or the amount of change in external environment temperature per unit time satisfy a predetermined condition, and interpolate the removed wrist temperature data to estimate the wrist temperature rhythm data in which the influence of external environment temperature is corrected.

Figure 6:
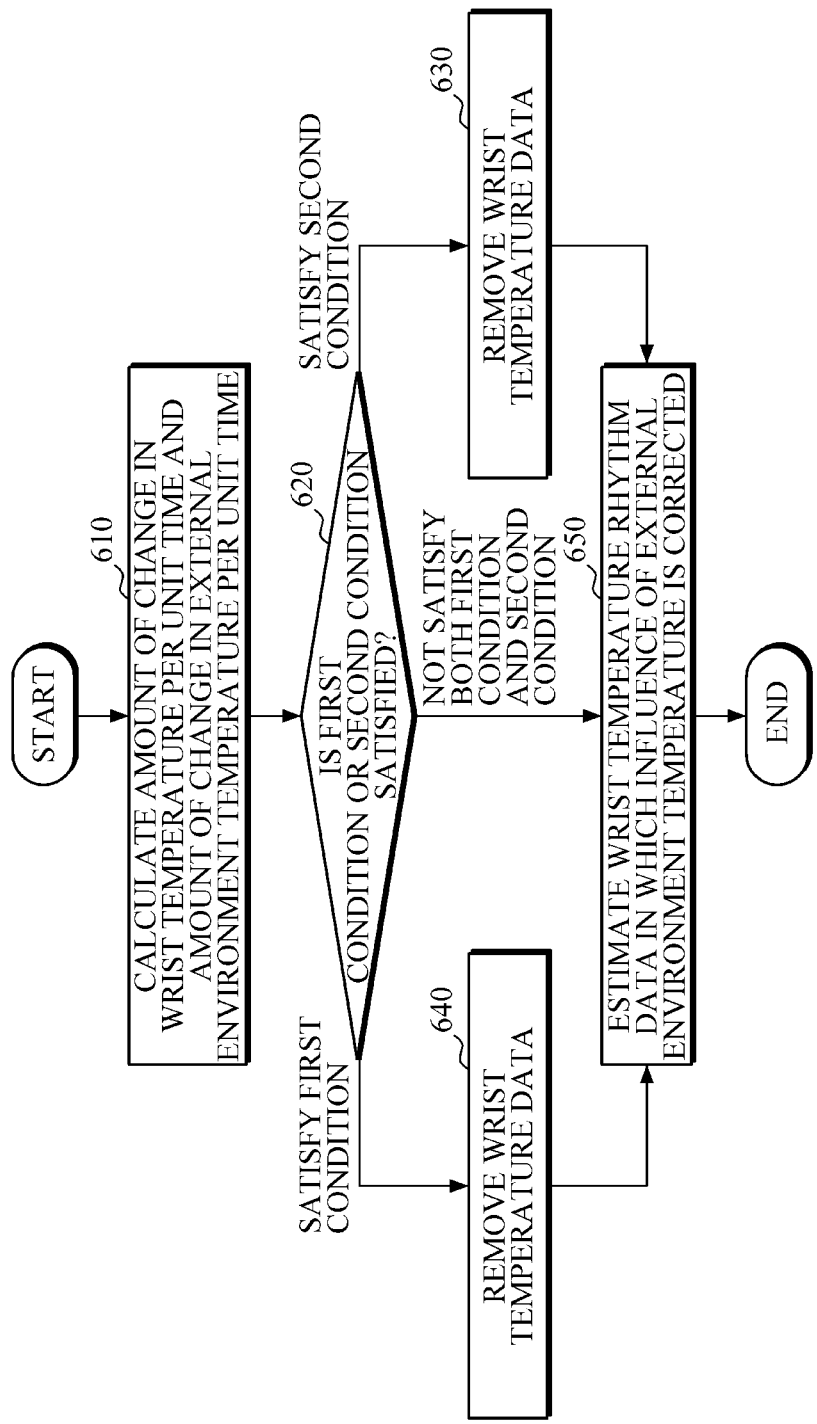
FIG. 6 is a flowchart illustrating a process of estimating wrist temperature rhythm data in which an influence of an external environment temperature is corrected, according to an example embodiment.

FIG. 6 is a flowchart illustrating a process of estimating wrist temperature rhythm data in which an influence of an external environment temperature is corrected, according to an example embodiment.

Referring to FIGS. 1 and 6, the wrist temperature rhythm acquisition apparatus 100 estimates or calculates the amount of change in wrist temperature per unit time on the basis of wrist temperature data, and the amount of change in external environment temperature per unit time on the basis of external environment temperature data, as depicted in 610. In this case, the unit time may be 1 minute, which is an example embodiment, and may not be limited thereto. That is, the unit time may be set to various values, such as 2 minutes, 5 minutes, 1 hour, and the like, according to the performance or purpose of a system.

The wrist temperature rhythm acquisition apparatus 100 determines whether the amount of change in wrist temperature per unit time and the amount of change in external environment temperature per unit time satisfy a first condition or a second condition, as depicted in 620. When the first condition is satisfied, the method proceeds to 640. When the second condition is satisfied, the method proceeds to 630. When neither the first condition nor the second condition is satisfied, the method proceeds to 650.

According to an example embodiment, the first condition may be that the amount of change in wrist temperature per unit time is less than a first threshold and the amount of change in external environment temperature per unit time that corresponds to the amount of change in wrist temperature per unit time is less than a second threshold, or that the amount of change in wrist temperature per unit time exceeds a third threshold and the amount of change in external environment temperature per unit time that corresponds to the amount of change in wrist temperature per unit time exceeds a fourth threshold. In this case, the first threshold may be 0, the second threshold may be 0.1, the third threshold may be 0, and the fourth threshold may be 0.2, but these are only examples, and the thresholds are not limited thereto. That is, the first to fourth thresholds may be set to various values according to the unit of time and the performance or purpose of the system.

According to an example embodiment, the second condition may be that an absolute value of the amount of change in external environment temperature per unit time exceeds a fifth threshold. In this case, the fifth threshold may be 0.9, which is an example embodiment, and is not limited thereto. That is, the fifth threshold may be set to various values according to the unit of time and the performance or purpose of the system.

The wrist temperature rhythm acquisition apparatus 100 removes wrist temperature data in a predetermined range when the amount of change in wrist temperature per unit time and the amount of change in external environment temperature per unit time satisfy the first condition, as depicted in 640.

For example, when the amount of change in wrist temperature per unit time and the amount of change in external environment temperature per unit time satisfy the first condition, the wrist temperature rhythm acquisition apparatus 100 may remove the wrist temperature data in the relevant unit time from the entire wrist temperature data, remove the wrist temperature data in a first time range after a reference time point for calculating the amount of change from the entire wrist temperature data, or remove the wrist temperature data in the first time range before and after the reference time point for calculating the amount of change from the entire wrist temperature data. In this case, the first time range may be five minutes, which is an example embodiment, and may not be limited thereto. That is, the first time range may be set to various values according to the unit of time and the performance or purpose of the system.

In 630, the wrist temperature rhythm acquisition apparatus 100 removes wrists temperature data in a predetermined range when the amount of change in external environment temperature per unit time satisfies a second condition.

For example, when the amount of change in external environment temperature per unit time satisfies a second condition, the wrist temperature rhythm acquisition apparatus 100 may remove wrists temperature data in a second time range after the reference time point for calculating the amount of change, or remove the wrist temperature data in the second time range before and after the reference time point for calculating the amount of change. In this case, the second time range may be 30 minutes, which is an example embodiment, and may not be limited thereto. That is, the second time range may be set to various values according to the unit of the time and the performance or purpose of the system.

The wrist temperature rhythm acquisition apparatus 100 interpolates the removed wrist temperature data and estimates the wrist temperature rhythm data in which the influence of the external environment temperature is corrected, as depicted in 650. For example, the wrist temperature rhythm acquisition apparatus 100 may interpolate the removed wrist temperature data on the basis of the remaining wrist temperature data resulting from the removal. In this case, the wrist temperature rhythm acquisition apparatus 100 may use various interpolation techniques, such as linear interpolation, double linear interpolation, parabolic interpolation, polynomial interpolation, spline interpolation, and the like.

In 650, when the amount of change in wrist temperature per unit time and the amount of change in external environment temperature per unit time do not satisfy the first condition and the second condition, the wrist temperature rhythm acquisition apparatus 100 determines that the external environment temperature has no influence on the wrist temperature data, and estimates the wrist temperature data as the wrist temperature rhythm data, as depicted in 650.

Figure 7:
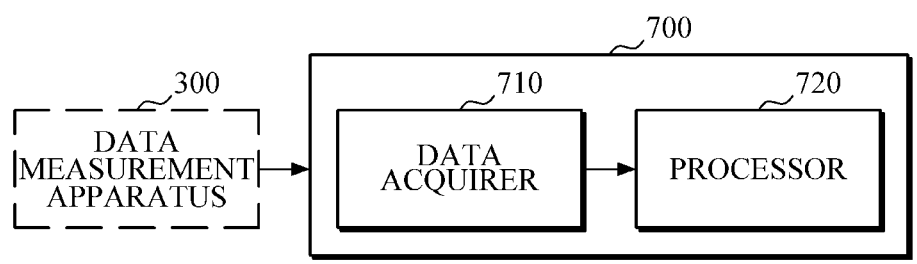
FIG. 7 is a block diagram illustrating a core temperature rhythm acquisition apparatus according to an example embodiment.

FIG. 7 is a block diagram illustrating a core temperature rhythm acquisition apparatus 700 according to an example embodiment. The core temperature rhythm acquisition apparatus 700 may be an apparatus for estimating a wrist temperature rhythm in which the influence of external environment temperature is corrected and acquiring a core temperature rhythm on the basis of the wrist temperature rhythm. The core temperature rhythm acquisition apparatus 700 may be implemented by a software module or manufactured in the form of a hardware chip, and be mounted in an electronic device. In this case, the electronic device may include a mobile phone, a smartphone, a tablet computer, a notebook computer, a PDA, a PMP, a navigation system, an MP3 player, a digital camera, a wearable device, etc. The type of wearable device may include a wristwatch type, a wrist band type, a belt type, a necklace type, an ankle band type, a thigh band type, a forearm band type, etc. However, the electronic device may not be limited to the above example, and the wearable device may also not be limited to the above example.

Referring to FIG. 7, the core temperature rhythm acquisition apparatus 700 includes a data acquirer 710 and a processor 720.

The data acquirer 710 may obtain the wrist temperature data of a user, external environment temperature data, the user's heart rate data, and data about the amount of exercise that the user carried out. The data about the amount of exercise may include activity data, position data, and the like.

According to an example embodiment, the data acquirer 710 may receive the wrist temperature data of the user, the external environment temperature data, the user's heart rate data, and the data about the amount of exercise the user carried out from a data measurement apparatus 300.

The processor 720 may estimate the wrist temperature rhythm data in which the influence of external environment temperature is corrected on the basis of the wrist temperature data and the external environment temperature data. For example, the processor 720 may remove the wrist temperature data in a predetermined range from the entire wrist temperature data on the basis of whether the amount of change in wrist temperature per unit time and/or the amount of change in external environment temperature per unit time satisfy a predetermined condition. The processor 720 may further interpolate the removed wrist temperature data to estimate the wrist temperature rhythm data in which the influence of external environment temperature is corrected.

The processor 720 may estimate the core temperature rhythm data on the basis of the estimated wrist temperature rhythm data and the acquired heart rate data and data about the amount of exercise.

The processor 720 will be described below in more detail with reference to FIG. 8.

The data measurement apparatus 300 may measure the user's wrist temperature data, the external environment temperature data, the user's heart rate data, and the data about the amount of exercise that the user carried out in response to a control signal generated according to a user input or a control signal received from the core temperature rhythm acquisition apparatus 700. The data measurement apparatus 300 may be a wearable device that may be worn on the user's body part, which is an example, and the data measurement apparatus 300 is not limited thereto.

Figure 8:
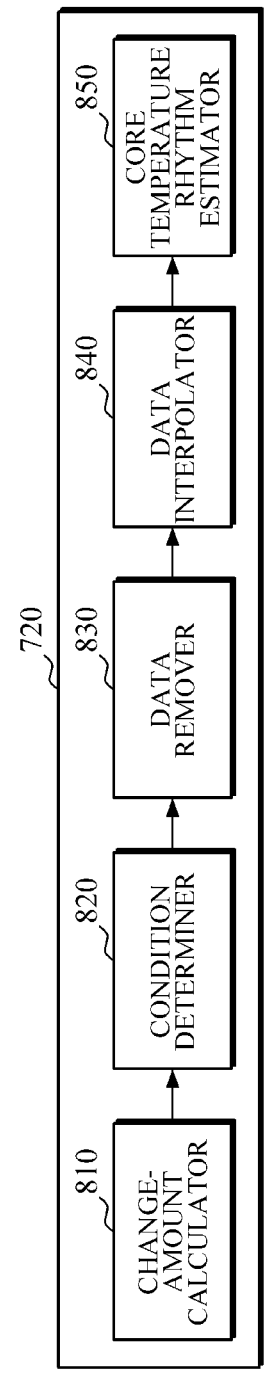
FIG. 8 is a block diagram illustrating a processor according to an example embodiment.

FIG. 8 is a block diagram illustrating the processor 720 according to an example embodiment.

Referring to FIG. 8, the processor 720 includes a change-amount calculator 810, a condition determiner 820, a data remover 830, a data interpolator 840, and a core temperature rhythm estimator 850. In this case, the change-amount calculator 810, the condition determiner 820, the data remover 830, and the data interpolator 840 are, respectively, the same as the change-amount calculator 210, the condition determiner 220, the data remover 230, and the data interpolator 240 of FIG. 2, and the detailed descriptions thereof will be omitted.

The core temperature rhythm estimator 850 may estimate the core temperature rhythm data on the basis of estimated wrist temperature rhythm data and acquired heart rate data and data about the amount of exercise. For example, the core temperature rhythm estimator 850 may estimate the core temperature rhythm data using a core temperature rhythm estimation model previously generated. In this case, the core temperature rhythm estimation model may be generated though machine learning on the basis of core temperature rhythm training data, wrist temperature rhythm training data that corresponds to the core temperature rhythm training data, heart rate training data, and exercise-amount training data.

A machine learning algorithm may include any one or any combination of a neural network, a decision tree, a genetic algorithm, genetic programming, a k-nearest neighbor algorithm, a radial basis function network, random forest, a support vector machine, deep learning, etc.

Figure 9:
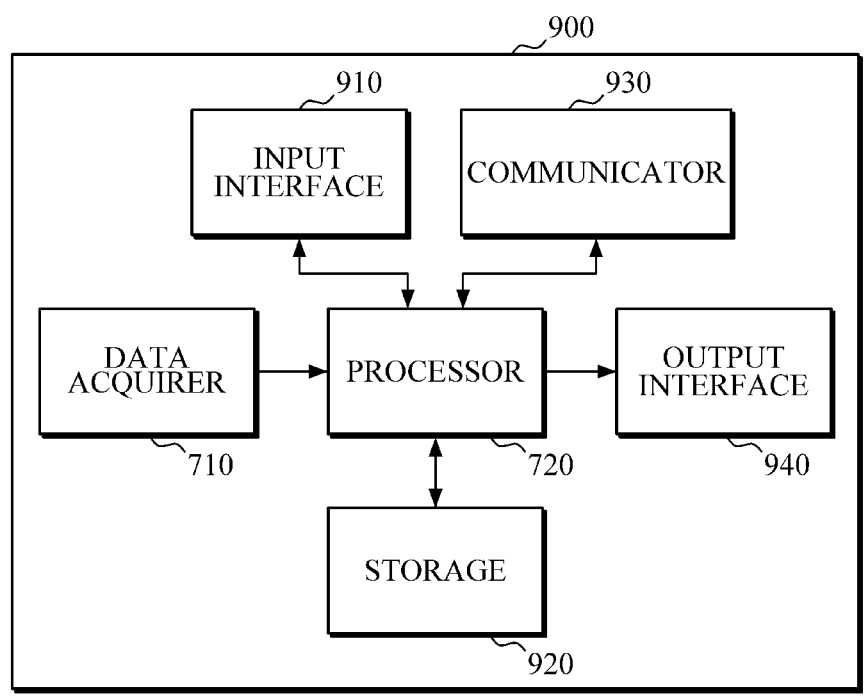
FIG. 9 is a block diagram illustrating a core temperature rhythm apparatus according to another example embodiment.

FIG. 9 is a block diagram illustrating a core temperature rhythm apparatus 900 according to another example embodiment.

Referring to FIG. 9, the core temperature rhythm acquisition apparatus 900 includes an input interface 910, a storage 920, a communicator 930, an output interface 940, a data acquirer 710, and a processor 720. In this case, the data acquirer 710 and the processor 720 are the same as those described with reference to FIG. 7, and the detailed descriptions thereof will be omitted.

The input interface 910 may receive various operation signals from a user. According to an example embodiment, the input interface 910 may include a key pad, a dome switch, a touch pad (resistive/capacitive), a jog switch, an H/W button, and the like. When the touch pad forms a mutual layer structure with a display, it may be referred to as a touch screen.

The storage 920 may store a program or instructions for operations of the core temperature rhythm acquisition apparatus 900 and may store data input to and/or output from the core temperature rhythm acquisition apparatus 900. In addition, the storage 920 may store wrist temperature data, external environment temperature data, the user's heart rate data, and the data about the amount of exercise carried out by the user that are obtained through the data acquirer 710, the amount of change in wrist temperature per unit time and the amount of change in external environment temperature per unit time that are calculated by the processor 720, and wrist temperature rhythm data and core temperature rhythm data that are estimated by the processor 720, and so on.

The communicator 930 may communicate with an external device. For example, the communicator 930 may transmit the data input from the user through the input interface 910 and the wrist temperature rhythm data and core temperature rhythm data that are estimated by the processor 720 to the external device, and may receive various data helpful for the estimation of wrist temperature rhythm data from the external device.

Although the data acquirer 710 and the communicator 930 are illustrated as separate elements in the example of FIG. 9 the data acquirer 710 and the communicator 930 may be integrated into one element.

The output interface 940 may output a result of the estimation of core temperature rhythm data. According to an example embodiment, the output interface 940 may output the result of the estimation of wrist temperature rhythm data and the like in any one or any combination of audible, visual, or tactile manners.

Figure 10:
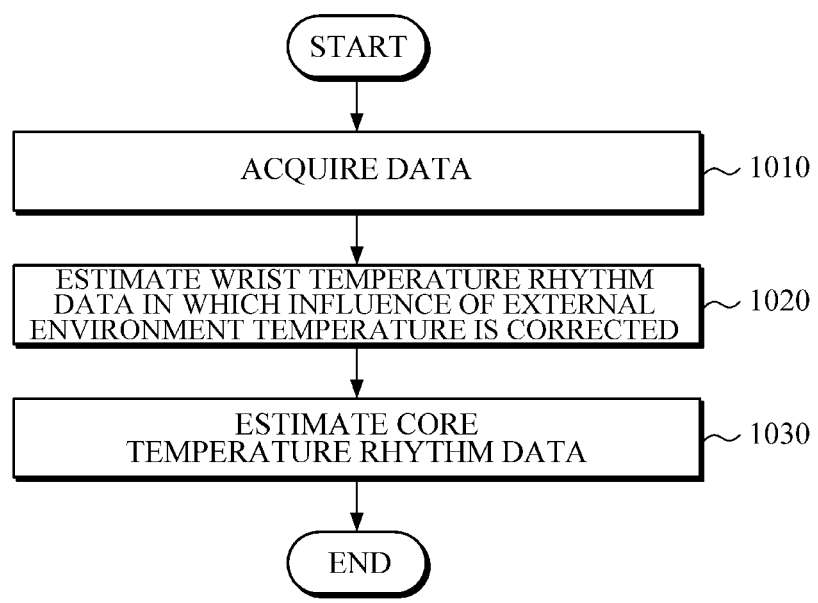
FIG. 10 is a flowchart illustrating a method of acquiring a core temperature rhythm, according to an example embodiment.

FIG. 10 is a flowchart illustrating a method of acquiring a core temperature rhythm, according to an example embodiment.

Referring to FIGS. 7 and 10, the core temperature rhythm acquisition apparatus 700 acquires the wrist temperature data of a user, external environment temperature data, the user's heart rate data, and data about the amount of exercise that the user carried out, as depicted in 1010. According to an example embodiment, the core temperature rhythm acquisition apparatus 700 may receive the wrist temperature data of the user, the external environment temperature data, the user's heart rate data, and the data about the amount of exercise the user carried out from a data measurement apparatus 300.

The core temperature rhythm acquisition apparatus 700 estimates wrist temperature rhythm data in which the influence of external environment temperature is corrected on the basis of wrist temperature data and external environment temperature data, as depicted in 1020. For example, the core temperature rhythm acquisition apparatus 700 may remove the wrist temperature data in a predetermined range from the entire wrist temperature data on the basis of whether the amount of change in wrist temperature per unit time and/or the amount of change in external environment temperature per unit time satisfy a predetermined condition, and interpolate the removed wrist temperature data to estimate the wrist temperature rhythm data in which the influence of external environment temperature is corrected.

The core temperature rhythm acquisition apparatus 700 estimates the core temperature rhythm data on the basis of the estimated wrist temperature rhythm data, acquired heart rate data, and data about the amount of exercise, as depicted in 1030. For example, the core temperature rhythm acquisition apparatus 700 may estimate the core temperature rhythm data, using a core temperature rhythm estimation model previously generated.

Figure 11:
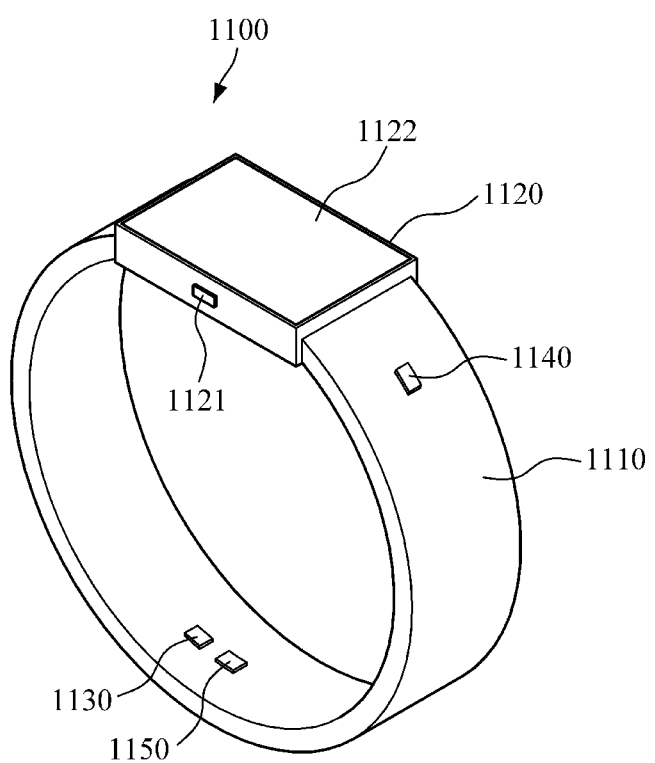
FIG. 11 is a perspective view illustrating a wrist-wearable device according to an example embodiment.
Figure 12:
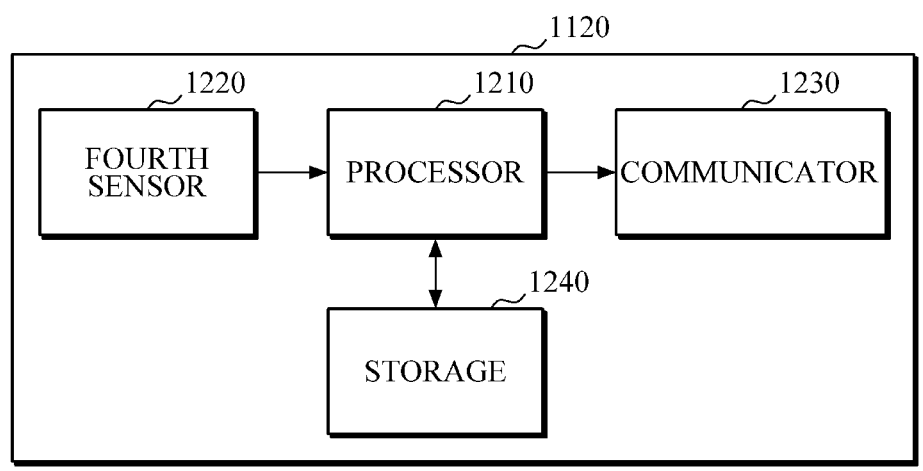
FIG. 12 is a block diagram illustrating elements mounted in a main body of a wrist-wearable device, according to an example embodiment.

FIG. 11 is a perspective view illustrating a wrist-wearable device 1100 according to an example embodiment, and FIG. 12 is a block diagram illustrating elements mounted in a main body 1120 of the wrist-wearable device 1100, according to an example embodiment. As shown in FIGS. 11 and 12, the above-described example embodiments of the wrist temperature rhythm acquisition apparatus and/or the core temperature rhythm acquisition apparatus may be mounted in the wrist-wearable device 1100.

Referring to FIGS. 11 and 12, the wrist-wearable device 1100 includes a strap 1110, the main body 1120, a first sensor 1130, and a second sensor 1140.

The strap 1110 may be configured in the form of a flexible band. However, this is an example embodiment, and the type of strap is not limited to the flexible band. That is, the strap may be composed of a plurality of strap members configured to be bent in such a manner that each strap member is wrapped around the user's wrist.

The first sensor 1130 may sense wrist temperature data of the user. According to an example embodiment, the first sensor 1130 may be disposed on one side of the strap 1110 that is in close or proximate contact with the user's wrist when the wrist-wearable device 1100 is worn. For example, the first sensor 1130 may be disposed at a portion of the strap 1110 that is close to the radial artery of the user's wrist when the wrist-wearable device 1100 is worn.

The second sensor 1140 may sense external environment temperature data. According to an example embodiment, the second sensor 1140 may be disposed on a side of the strap 1110 that is not in close or proximate contact with the user's wrist when the wrist-wearable device 1100 is worn.

The main body 1120 may have a processor 1210 inside thereof.

The processor 1210 may estimate wrist temperature rhythm data in which the influence of external environment temperature is corrected on the basis of the wrist temperature data and the external environment temperature data. For example, the processor 1210 may remove the wrist temperature data in a predetermined range from the entire wrist temperature data on the basis of whether the amount of change in wrist temperature per unit time and/or the amount of change in external environment temperature per unit time satisfy a predetermined condition, and interpolates the removed wrist temperature data to estimate the wrist temperature rhythm data in which the influence of external environment temperature is corrected.

In addition, the processor 1210 may estimate the core temperature rhythm data on the basis of the estimated wrist temperature rhythm data and acquired heart rate data and data about the amount of exercise. For example, the processor 1210 may estimate the core temperature rhythm data using a core temperature rhythm estimation model previously generated. In this case, the core temperature rhythm estimation model may be generated though machine learning on the basis of core temperature rhythm training data, wrist temperature rhythm training data that corresponds to the core temperature rhythm training data, heart rate training data, and exercise-amount training data.

The wrist-wearable device 1100 may further include an input interface 1121 and a display 1122 that are mounted in the main body 1120. The input interface 1121 may receive various operation signals from the user. The display 1122 may display data processed by the processor 1210, processing result data, and the like.

The wrist-wearable device 1100 may further include a third sensor 1150, a fourth sensor 1220, a communicator 1230, and a storage 1240.

The third sensor 1150 may sense the heart rate data of the user. According to an example embodiment, the third sensor 1150 may be disposed on one side of the strap 1110 that is in close or proximate contact with the user's wrist when the wrist-wearable device 1100 is worn. For example, the third sensor 1150 may be disposed at a portion of the strap 1110 that is close to the radial artery of the user's wrist when the wrist-wearable device 1100 is worn.

The fourth sensor 1220 may be mounted in the main body 1120 and sense data about the amount of exercise that the user carried out. The data about the amount of exercise may include activity data, position data, and the like.

The communicator 1230 may be equipped in the main body 1120 and communicate with an external device. For example, the communicator 1230 may transmit data input by the user through the input interface 1121, the data processed by the processor 1210, the processing result data, and the like to the external device, or may receive various types of data helpful for data processing from the external device.

The storage 1240 may store a program or instructions for operations of the wrist-wearable device 1100, and may store data input to and/or output from the wrist-wearable device. In addition, the storage 1240 may store the data processing result of the processor 1210.

The example embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A core temperature rhythm acquisition apparatus comprising:
    a data acquirer configured to acquire wrist temperature data of a user, external environment temperature data, heart rate data of the user, and data of an amount of exercise that the user carried out; and
    a processor configured to:
        determine an amount of change in a wrist temperature from a first time point to a second time point and an amount of change in an external environment temperature from the first time point to the second time point, based on the acquired wrist temperature data and the acquired external environment temperature data;
        determine whether a first condition is satisfied;
        determine whether a second condition is satisfied;
        in response to determining that the first condition is satisfied, remove first wrist temperature data, in a first time range after a reference point for determining the amount of change in the wrist temperature, from the acquired wrist temperature data to generate remaining wrist temperature data;
        in response to determining that the second condition is satisfied, remove second wrist temperature data, in a second time range, that is different than the first time range, after the reference point for determining the amount of change in the wrist temperature, from the acquired wrist temperature data to generate the remaining wrist temperature data;
        estimate wrist temperature rhythm data in which an influence of the external environment temperature is corrected by interpolating the removed first wrist temperature data or the removed second wrist temperature data based on the remaining wrist temperature data; and
        estimate core temperature rhythm data, based on the estimated wrist temperature rhythm data, the acquired heart rate data, and the acquired data of the amount of exercise,
    wherein the first condition is that the amount of change in the wrist temperature is less than a first threshold and the amount of change in the external environment temperature is less than a second threshold that is different than the first threshold, or that the amount of change in the wrist temperature is greater than a third threshold and the amount of change in the external environment temperature is greater than a fourth threshold that is different than the third threshold, and
    wherein the second condition is that an absolute value of the amount of change in the external environment temperature is greater than a fifth threshold.

2. The core temperature rhythm acquisition apparatus of claim 1, wherein the processor is further configured to estimate the core temperature rhythm data, using a core temperature rhythm estimation model.

3. The core temperature rhythm acquisition apparatus of claim 2, wherein the core temperature rhythm estimation model is generated through machine learning based on core temperature rhythm training data, wrist temperature rhythm training data corresponding to the core temperature rhythm training data, heart rate training data, and training data of an amount of exercise.

4. The core temperature rhythm acquisition apparatus of claim 3, wherein the machine learning comprises any one or any combination of a neural network, a decision tree, a genetic algorithm, genetic programming, a k-nearest neighbor algorithm, a radial basis function network, a random forest, a support vector machine, and deep learning.

5. A method comprising:
acquiring wrist temperature data of a user, external environment temperature data, heart rate data of the user, and data of an amount of exercise that the user carried out;
determining an amount of change in a wrist temperature from a first time point to a second time point and an amount of change in an external environment temperature from the first time point to the second time point, based on the acquired wrist temperature data and the acquired external environment temperature data;
determining whether a first condition is satisfied;
determining whether a second condition is satisfied;
in response to determining that the first condition is satisfied, removing first wrist temperature data, in a first time range after a reference point for determining the amount of change in the wrist temperature, from the acquired wrist temperature data to generate remaining wrist temperature data;
in response to determining that the second condition is satisfied, removing second wrist temperature data, in a second time range, that is different than the first time range, after the reference point for determining the amount of change in the wrist temperature, from the acquired wrist temperature data to generate the remaining wrist temperature data;
estimating wrist temperature rhythm data in which an influence of the external environment temperature is corrected by interpolating the removed first wrist temperature data or the removed second wrist temperature data based on the remaining wrist temperature data; and
estimating core temperature rhythm data, based on the estimated wrist temperature rhythm data, the acquired heart rate data, and the acquired data of the amount of exercise,
wherein the first condition is that the amount of change in the wrist temperature is less than a first threshold and the amount of change in the external environment temperature is less than a second threshold that is different than the first threshold, or that the amount of change in the wrist temperature is greater than a third threshold and the amount of change in the external environment temperature is greater than a fourth threshold that is different than the third threshold,
wherein the second condition is that an absolute value of the amount of change in the external environment temperature is greater than a fifth threshold,
wherein the estimating of the core temperature rhythm data comprises estimating the core temperature rhythm data, using a core temperature rhythm estimation model, and
wherein the core temperature rhythm estimation model is generated through machine learning based on core temperature rhythm training data, wrist temperature rhythm training data corresponding to the core temperature rhythm training data, heart rate training data, and training data of an amount of exercise.

6. A wrist-wearable device comprising:
a first sensor configured to sense wrist temperature data of a user;
a second sensor configured to sense external environment temperature data;
a third sensor configured to sense heart rate data of the user;
a fourth sensor configured to sense data of an amount of exercise that the user carried out; and
a processor configured to:
determine an amount of change in a wrist temperature from a first time point to a second time point and an amount of change in an external environment temperature from the first time point to the second time point, based on the sensed wrist temperature data and the sensed external environment temperature data;
determine whether a first condition is satisfied;
determine whether a second condition is satisfied;
in response to determining that the first condition is satisfied, remove first wrist temperature data, in a first time range after a reference point for determining the amount of change in the wrist temperature, from the sensed wrist temperature data to generate remaining wrist temperature data;
in response to determining that the second condition is satisfied, remove second wrist temperature data, in a second time range, that is different than the first time range, after the reference point for determining the amount of change in the wrist temperature, from the sensed wrist temperature data to generate the remaining wrist temperature data;
acquire wrist temperature rhythm data in which an influence of the external environment temperature is corrected by interpolating the removed first wrist temperature data or the removed second wrist temperature data based on the remaining wrist temperature data; and
acquire core temperature rhythm data, based on the acquired wrist temperature rhythm data, the sensed heart rate data, and the sensed data of the amount of exercise,
wherein the first condition is that the amount of change in the wrist temperature is less than a first threshold and the amount of change in the external environment temperature is less than a second threshold that is different than the first threshold, or that the amount of change in the wrist temperature is greater than a third threshold and the amount of change in the external environment temperature is greater than a fourth threshold that is different than the third threshold,
wherein the second condition is that an absolute value of the amount of change in the external environment temperature is greater than a fifth threshold,
wherein the processor is further configured to acquire the core temperature rhythm data, using a core temperature rhythm estimation model, and
wherein the core temperature rhythm estimation model is generated through machine learning based on core temperature rhythm training data, wrist temperature rhythm training data corresponding to the core temperature rhythm training data, heart rate training data, and training data of an amount of exercise.

7. The wrist-wearable device of claim 6, wherein the first sensor is disposed on a surface of the wrist-wearable device in proximate contact with a wrist of the user when the wrist-wearable device is worn by the user.

8. The wrist-wearable device of claim 6, wherein the second sensor is disposed on a surface of the wrist-wearable device that is not in proximate contact with a wrist of the user when the wrist-wearable device is worn by the user.

9. An apparatus comprising:
   a first sensor configured to sense user temperatures;
   a second sensor configured to sense external environment temperatures;
   a third sensor configured to sense heart rates of the user;
   a fourth sensor configured to sense amounts of exercise that the user carried out; and
   a processor configured to:
      determine an amount of change in a user temperature from a first time point to a second time point and an amount of change in an external environment temperature from the first time point to the second time point, based on the sensed user temperatures and the sensed external environment temperatures;
      determine whether the amount of change in the user temperature is less than a first threshold and the amount of change in the external environment temperature is less than a second threshold that is different than the first threshold, the amount of change in the user temperature is greater than a third threshold and the amount of change in the external environment temperature is greater than a fourth threshold that is different than the third threshold, or an absolute value of the amount of change in the external environment temperature is greater than a fifth threshold;
      in response to determining that the amount of change in the user temperature is less than the first threshold and the amount of change in the external environment temperature is less than the second threshold that is different than the first threshold, or that the amount of change in the user temperature is greater than the third threshold and the amount of change in the external environment temperature is greater than the fourth threshold that is different than the third threshold, remove first user temperatures, in a first time range after a reference point for determining the amount of change in the user temperature, from the sensed user temperatures to generate remaining user temperatures;
      in response to determining that the absolute value of the amount of change in the external environment temperature is greater than the fifth threshold, remove second user temperatures, in a second time range, that is different than the first time range, after the reference point for determining the amount of change in the user temperature, from the sensed user temperatures to generate the remaining user temperatures;
      interpolate, into the remaining user temperatures, third user temperatures replacing the removed first user temperatures or the removed second user temperatures, based on the remaining user temperatures, to generate user temperature rhythm data; and
      generate core temperature rhythm data, based on the generated user temperature rhythm data, the sensed heart rates, and the sensed amounts of exercise.

* * * * *